(12) United States Patent
Geerke et al.

(10) Patent No.: US 6,452,133 B1
(45) Date of Patent: Sep. 17, 2002

(54) APPARATUS AND METHODS FOR ALTERNATING LASER TREATMENT OF PHARMACEUTICAL DISPENSERS

(75) Inventors: Johan H. Geerke, Los Altos; Keith Perry Minton, San Jose, both of CA (US)

(73) Assignee: Alza Corporation, Mountain View, CA (US)

( * ) Notice: Subject to any disclaimer, the term of this patent is extended or adjusted under 35 U.S.C. 154(b) by 0 days.

(21) Appl. No.: 09/616,822

(22) Filed: Jul. 14, 2000

Related U.S. Application Data
(60) Provisional application No. 60/145,592, filed on Jul. 26, 1999.

(51) Int. Cl.$^7$ .............................................. B23K 26/08
(52) U.S. Cl. ............................ 219/121.82; 219/121.71
(58) Field of Search ..................... 219/121.7, 121.71, 219/121.74, 121.82, 121.76, 384, 158, 121.8, 121.81; 424/467

(56) References Cited

U.S. PATENT DOCUMENTS

| | | | |
|---|---|---|---|
| 3,828,972 A | * | 8/1974 | Bender |
| 4,063,064 A | | 12/1977 | Saunders et al. |
| 4,088,864 A | | 5/1978 | Theeuwes et al. |
| 4,349,719 A | * | 9/1982 | Cashwell |
| 4,499,362 A | * | 2/1985 | Martin |
| 4,524,785 A | * | 6/1985 | Seragnoli et al. |
| 5,148,818 A | * | 9/1992 | Arthur |
| 5,375,613 A | * | 12/1994 | Aindow et al. |
| 5,658,474 A | | 8/1997 | Geerke |
| 5,690,125 A | * | 11/1997 | Niemann et al. |
| 5,698,119 A | | 12/1997 | Geerke |
| 5,701,725 A | * | 12/1997 | Neri et al. |
| 6,070,592 A | * | 6/2000 | Rizzoli et al. |
| 6,167,684 B1 | * | 1/2001 | Perrone |
| 6,185,901 B1 | * | 2/2001 | Aylward |

FOREIGN PATENT DOCUMENTS

WO    WO98/26898    6/1998

* cited by examiner

Primary Examiner—M. Alexandra Elve
Assistant Examiner—Jonathan Johnson
(74) Attorney, Agent, or Firm—Samuel Webb

(57) ABSTRACT

Methods and apparatus for laser treating batches of pharmaceutical dispensers are provided. Sequential batches of untreated dispensers are carried on alternate batch carriers that are advanced into associated alternate stationary laser treatment stations. The multiple stationary laser treatment stations are located within a region of adjacency in which a single laser source can be operated to treat alternate batches of dispensers positioned within the associated alternate laser treatment stations. A laser controller directs the laser beam to alternatingly operate in each laser treatment station and, within each laser treatment station, to treat each dispenser in a batch of dispensers positioned therein. An advance coordinator advances the batch carriers in coordination with the activity of the laser controller in a repeating alternating cycle.

15 Claims, 5 Drawing Sheets

APPARATUS AND METHODS FOR ALTERNATING LASER TREATMENT OF PHARMACEUTICAL DISPENSERS

CROSS-REFERENCE TO RELATED APPLICATIONS

This application claims the priority of provisional application Serial No. 60/145,592 filed Jul. 26, 1999, which is incorporated herein by reference.

BACKGROUND OF THE INVENTION

1. Field of the Invention

This invention relates generally to processing of pharmaceutical dispensers wherein a processing step involves laser treatment of the dispensers. More particularly, this invention relates to methods and apparatus for providing alternating processing of pharmaceutical dispensers wherein advancement of batches of dispensers through a plurality of laser treatment stations is coordinated with controlling a laser for treating the dispensers in the laser treatment stations.

2. Description of the Related Art Including Information Disclosed Under 37 CFR 1.97 and 1.98

Some pharmaceutical dispensers are constructed with a wall or membrane surrounding an internal compartment containing the active drug ingredient which, following administration of the dispenser, is released through an opening or openings formed through the wall. The size, shape and location(s) of the opening(s) may vary in accord with the particular requirements of the dispenser. The wall material may itself contain pores which serve as the openings or self-forming pores can arise from the use of certain components within the wall that can be dissolved, leached, eroded or extracted by a fluid environment to thereby permit drug release therethrough following administration of the dispenser. When the wall material does not contain or form openings, however, openings can be formed in a subsequent following administration of the dispenser. When the wall material does not contain or form openings, however, openings can be formed in a subsequent processing step involving mechanical drilling or laser ablation of the wall. Laser ablation may also be used to "scribe" or mark pharmaceutical dispensers.

Examples of methods and apparatus for laser drilling of pharmaceutical dispensers are described and claimed in the following US Patents, owned by ALZA Corporation: U.S. Pat. No. 4,063,064 and 4,088,864, each of which is incorporated in its entirety by reference herein. In addition, methods and apparatus for laser-forming delivery ports in pharmaceutical dispensers, including non-symmetric multi-layer osmotic dispensers, are claimed and described in U.S. Pat. Nos. 5,658,474 and 5,698,119, owned by Alza Corporation, each of which is incorporated in its entirety by reference herein.

Pharmaceutical dispensers to be treated by a laser are generally continuously advanced along a conveyer path that intersects a laser beam path. The dispensers are treated one at a time by laser energy at a drill site on the dispenser as each dispenser form moves through, or stops within, a laser treatment station in the area of intersection of the conveyer and the laser beam paths. The laser is activated during the time that a dispenser is moving through, or is stationary within, the laser treatment station and is inactivated during the time that the dispensers are advancing into and out of the laser treatment station. Thus, the laser is activated only intermittently, and may, in fact, spend more time inactivated than activated.

It would be an advance in the art to provide methods and apparatus for laser treatment of pharmaceutical dispensers that maximize the time during which the laser is activated to thereby increase the speed, efficiency and cost-effectiveness of laser treatment of pharmaceutical dispensers.

BRIEF SUMMARY OF THE INVENTION

The present invention pertains to providing improved methods and apparatus for treating pharmaceutical dispensers with a laser. The methods and apparatus of the present invention provide significant advantages including a higher dispenser treatment rate, less approach time per treated dispenser and more efficient use of the laser.

The methods and apparatus of the present invention provide for pharmaceutical dispensers to be treated in batches rather than singly. Sequential batches of untreated dispensers are carried on alternate batch carriers that are advanced into associated alternate stationary laser treatment stations. The multiple stationary laser treatment stations are located within a region of adjacency in which a single laser source can be operated to treat alternate batches of dispensers positioned within the associated alternate laser treatment stations. A laser controller directs the laser beam to alternatingly operate in each laser treatment station and, within each laser treatment station, to treat each dispenser in a batch of dispensers positioned therein. An advance coordinator advances the batch carriers in coordination with the activity of the laser controller in a repeating alternating cycle wherein one batch of untreated dispensers is held stationary in position within one laser treatment station (while the laser is operated in the one laser treatment station) during the time that another batch of untreated dispensers is being advanced into another laser treatment station. In this manner, a batch of untreated dispensers is substantially continuously positioned in one or another laser treatment station and the laser is optimally substantially continuously operating to treat dispensers within one or another of the laser treatment stations.

In another aspect, a substantially continuous supply of batches of untreated dispensers is provided to the batch carriers for sequential advancement into the laser treatment stations. Preferably, a dispenser distribution and supply system is provided that permits a supply backlog pressure to develop at on-load stations for each batch carrier. Suitable methods and apparatus for maintaining a substantially constant supply to the alternate batch carriers of the present invention can be provided, for example, with appropriate feedback monitoring and rate coordination logic circuitry provided at strategic locations between a central supply, a supply accumulator and the supply paths for each batch carrier.

The above-described features and advantages, as well as others, will become more apparent from the following detailed disclosure of the invention and the accompanying claims.

BRIEF DESCRIPTION OF THE SEVERAL VIEWS OF THE DRAWINGS

Further objects and advantages of the present invention will become apparent from the following detailed description and drawings (not drawn to scale) in which.

DETAILED DESCRIPTION OF THE INVENTION

Figure 1:
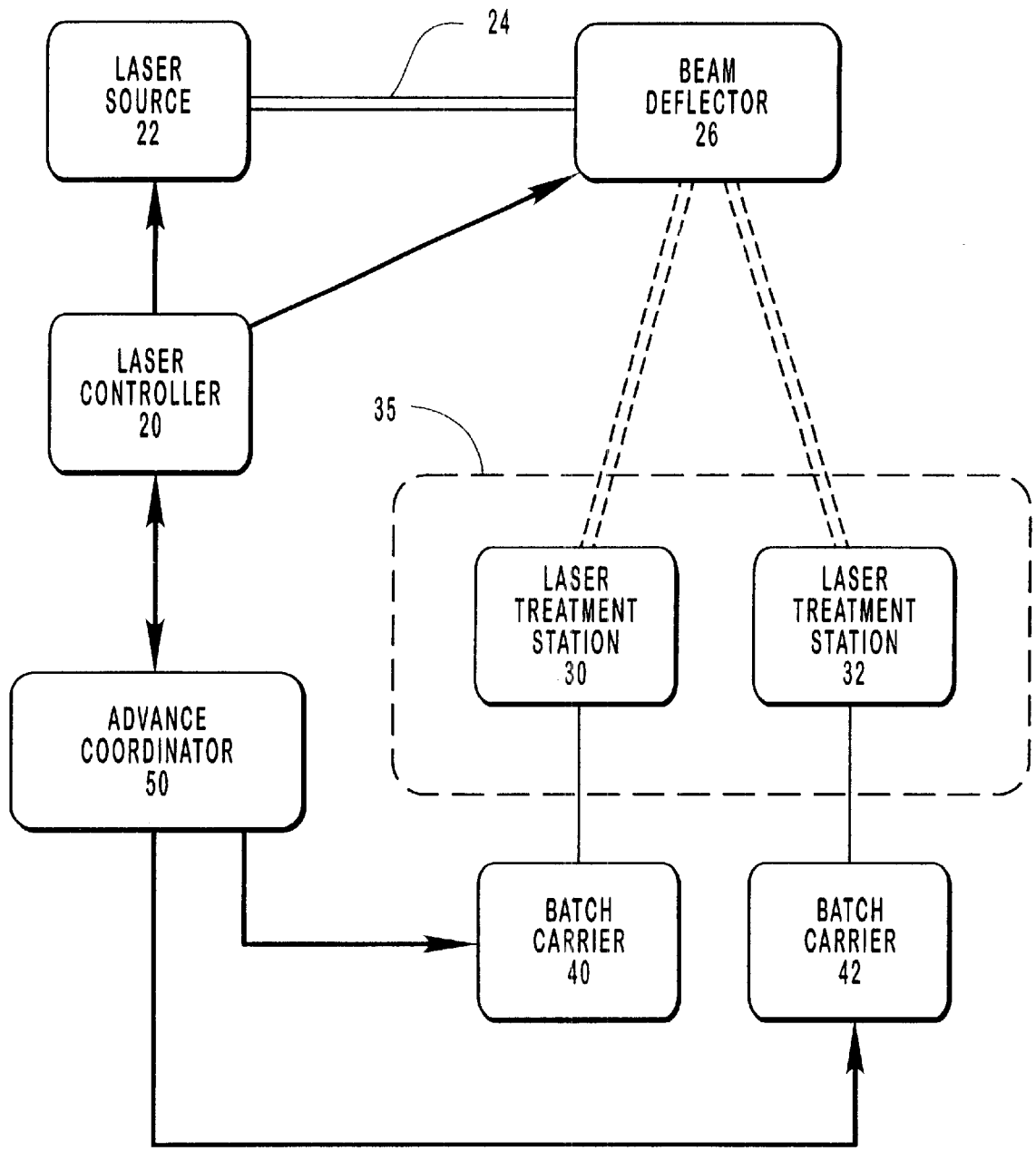
FIG. 1 is a schematic block diagram illustration of the alternating laser treatment in accord with the present invention.

The phrase "pharmaceutical dispenser" and the term "dispenser," as used herein, denote solid pharmaceutical dosage forms for delivering a beneficial agent such as a drug to a human or animal following administration of the dosage form. Such solid dosage forms include, e.g., dosage forms for swallowing, inserting into a body cavity, or implanting within a body.

The phrase "laser treatment" refers to exposing a pharmaceutical dispenser to a beam of laser energy to ablate, i.e., "burn," some portion of the exposed material which absorbs the laser energy.

The methods and apparatus of the invention are exemplified herein with reference to laser treatment of oral osmotic dosage forms to form at least one drug delivery port through a membrane surrounding an internal compartment of the dosage form. The internal compartment contains a drug in at least one layer and an expandable polymer in a "push" layer. Such osmotic dosage forms are typically manufactured by compressing the component drug-containing layer(s) and the push layer(s) together to form a core, applying the semipermeable membrane around the core and then drilling, typically with a laser, at least one delivery port. Following oral administration, fluid is imbibed through the semipermeable membrane causing the drug-containing layer to form a deliverable drug formulation and causing the polymer layer to expand and "push" the drug formulation through the delivery port(s). It will be appreciated by persons of skill in the art that other types of pharmaceutical dispensers, including conventional tablets and capsules, can readily be laser treated in accord with the methods and apparatus of the present invention as described and claimed herein.

As described in more detail below, the exemplary dispensers illustrated herein are capsule-shaped tablets that require the drug delivery port(s) to be drilled into one of the narrow rounded ends. As illustrated herein, the exemplary dispensers are preferably transported in transport pucks that securely retain the dispensers within a central bore and maintain the dispensers in a preferred attitude for laser treatment, i.e., with the small end of the dispenser containing the drill site for a drug delivery port facing upward and exposed for laser treatment. It will be appreciated that the transport pucks are optional and that other suitable means for securely transporting the dispensers may be used. In addition, the methods and apparatus of the present invention may be utilized for laser drilling of other types of dispensers having other configurations.

The methods and apparatus of the present invention are preferably utilized to treat pharmaceutical dispensers in batches containing a plurality of dispensers although it will be appreciated that a "batch" of dispensers may contain only one dispenser. Sequential batches of untreated dispensers are carried on alternate batch carriers that are advanced into associated stationary laser treatment stations. The multiple stationary laser treatment stations are located within a region of adjacency in which a single laser source can be operated to treat batches of dispensers positioned within each of the multiple laser treatment stations. A laser controller directs the laser beam to alternatingly operate in each laser treatment station and, within each laser treatment station, to treat each dispenser in a batch of dispensers positioned therein. An advance coordinator advances the batch carriers in coordination with the activity of the laser controller in a repeating alternating cycle wherein one batch of untreated dispensers is held stationary in position within one laser treatment station (while the laser is operated in the one laser treatment station) during the time that another batch of untreated dispensers is being advanced into another laser treatment station. In this manner, a batch of untreated dispensers is substantially continuously positioned in one or another laser treatment station and the laser is optimally substantially continuously operating to treat the dispensers.

As used herein, the phrases "one and another" and "one or another" are used to refer to a plurality of items that are alternately involved in the practice of the present invention, i.e., the present invention comprises a plurality of laser treatment stations wherein the laser alternatingly operates to treat alternate batches of untreated dispensers advanced into and out of the laser treatment stations on alternate batch carriers. The plurality of laser treatment stations, batches of dispensers and batch carriers may be two or more and the reference to "one or another" indicates alternating between any two different stations, any two different batches or any two different carriers whether the two different items are, e.g., a first and second item or a second and third item or a first and third item, etc. Similarly, the term "next" as used herein refers to any next item, e.g., any next batch of untreated dispensers in a sequence of batches, and is not limited to an immediately next item.

With reference to the above-described repeating alternating cycle, FIG. 1 provides a schematic block diagram description of the alternating laser treatment apparatus and method in accord with the present invention. As shown in FIG. 1, a laser source 22 for generating a laser beam 24 is associated with a laser beam controller 20 for activating and directing the laser beam. As known in the art, a beam deflector 26, controlled by the laser beam controller, is operated to direct the laser beam (as indicated by the dotted lines) to treat pharmaceutical dispensers located in at least one and another laser treatment stations, represented by boxes 30 and 32. Under control of the laser beam controller, the laser beam is preferably positioned to sequentially treat each dispenser treatment site on each dispenser within the laser treatment station by adjusting an optical structure in beam deflector 26. Alternatively, it will be appreciated by those of skill in the art that properly arranged and adapted equipment can be used to effect concurrent laser treatment of a plurality of dispensers, if desired. In any event, laser beam controller activates the laser source to provide a sequence of short bursts of laser energy, one or more burst for each dispenser treatment site, while the batch of dispensers to be treated is positioned within that laser treatment station.

As described above, the alternate laser treatment stations are located within a region of adjacency, represented by large dotted-line box 35, wherein the single laser source can be operated to treat dispensers in the alternate laser treatment stations. In general, the time required to treat a batch of dispensers in one laser treatment station is less than the time required to move another batch into another laser treatment station such that a single laser source, with appropriate beam deflection apparatus and controller means, can efficiently service more than one treatment station. Within the region of adjacency, the laser treatment stations are preferably symmetrical within a common focal plane with respect to the beam deflector to minimize the adjustments needed to treat dispensers in the alternate laser treatment stations. The proximity of the two laser treatment stations reduces the beam deflection required to move the beam back and forth between alternate laser treatment stations at the end of each laser treatment cycle. In addition, the proximity localizes the debris generated by the laser energy for easy collection by airflow through the laser treatment stations.

The batches of untreated dispensers are supplied to the laser treatment stations on associated batch carriers, represented by boxes 40 and 42. The beam of laser energy treats each dispenser in a batch of dispensers while the batch is held within a laser treatment station. The energy of the beam may discolor the surface of the dispenser by scorching, or remove some outer material by vaporization. This material removal may drill a hole (drug delivery port) of controlled bore diameter through the outer wall material of each dispenser. Alternatively, the energy may merely scribe the periphery of a larger port around a central plug. In either case, the drilling or scribing may extend completely or partially through the outer wall material by controlling the laser energy and exposure time of the dispenser.

The advance coordinator 50, utilizing appropriate logic circuitry, advances the batch carriers in coordination with the laser controller such that a batch of untreated dispensers is substantially continuously positioned in one or another laser treatment station for presentation to the laser beam during the time that another batch of untreated dispensers is advancing into another of the one or another laser treatment stations. In this manner, the laser is optimally substantially continuously operating to alternatingly treat batches of dispensers positioned in one or another laser treatment station and one or another of the batch carriers is alternatingly being advanced to position a batch of untreated dispensers in another of the one or another laser treatment stations. The batch carriers are advanced and stopped by ADVANCE and STOP commands from advance coordinator 50 to a suitable motive device (not shown) for advancing the batch carriers. It will be appreciated that the laser beam controller 20 and the advance coordinator 50 comprise appropriate logic circuitry that functions in coordination. It will be appreciated that the logic circuitry for performing the functions of both the laser beam controller and the advance coordinator may be combined within a single structural device or may be encompassed in separate devices appropriately connected to each other.

It will be appreciated that the alternate batch carriers may comprise any suitable structure for carrying sequential batches of dispensers into a laser treatment station, holding the dispensers within the laser treatment station, and carrying the treated dispensers out of the laser treatment station. For example, the batch carriers may comprise parallel linear conveyors having means for carrying dispensers arrayed in sequential batches thereon. Each conveyor is alternately advanced to position a batch of untreated dispensers in a laser treatment station, stopped to permit each dispenser to be laser treated in the laser treatment station and advanced again to move the treated dispensers out of the laser treatment station and position a next batch of untreated dispensers in the laser treatment station. Moreover, the activity of the two (or more) conveyors is coordinated such that when the one conveyor is advancing a batch of untreated dispensers into its associated laser treatment station, the other conveyor is stationary while a batch of dispensers is being treated in its associated laser treatment station.

As described in more detail below, the individual dispensers are arranged in batches and carried in an appropriate stable attitude with respect to the laser beam to permit accurate laser treatment of each dispenser, in sequence, while the batch is held stationary in the laser treatment station. In a presently preferred embodiment, the pharmaceutical dispensers are carried in transport pucks as described in more detail below. The actual number and configuration of dispensers in each batch is variable and depends on many factors including the size of the region of adjacency, the size and shape of the dispensers, the size of the batch carriers, etc., as will be appreciated by persons of skill in the art.

Figure 2:
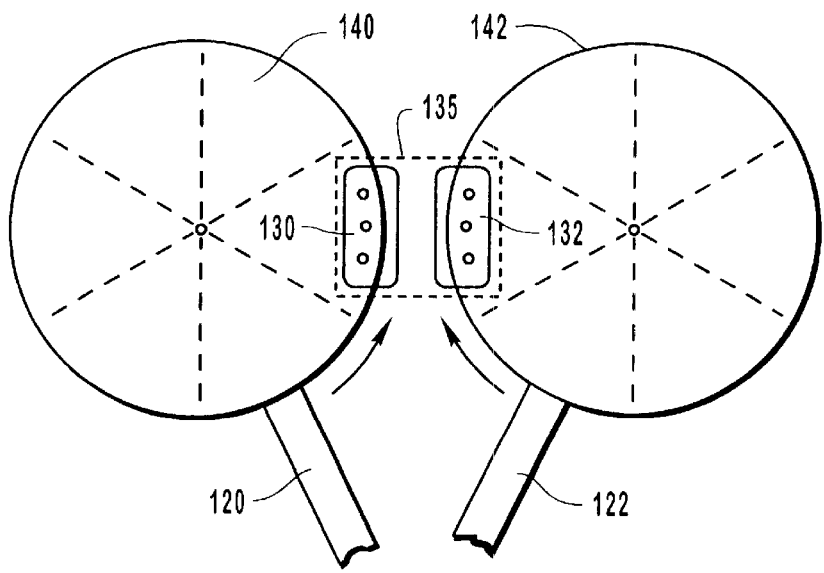
FIG. 2 is a partial plan view of a preferred embodiment of the present invention wherein the alternate batch carriers comprise alternate rotating wheels in accord with the present invention.

FIG. 2 shows a partial schematic plan view of a preferred embodiment of the present invention wherein the alternate batch carriers comprise alternate (one and another) rotating wheels, 140 and 142. The wheels are proximally positioned such that each wheel carries sequential batches of untreated dispensers through a region of adjacency, represented by dotted-line box 135, wherein a single laser source (not shown) can be operated to alternatingly treat dispensers in each of the laser treatment stations, 130 and 132, encompassed therein (illustrated as boxes overlying a portion of each wheel). For illustration purposes, in FIG. 2, the circles within the laser treatment stations represent exemplary laser treatment sites where individual dispensers (not shown) are to be positioned during laser treatment. It will be appreciated that the laser source (not shown) and beam deflector (not shown) are suitably located with respect to the laser treatment stations to provide laser treatment of each individual dispenser within a batch of untreated dispensers while that batch is positioned within one of the laser treatment stations.

From FIG. 2, it can be seen that rotation of the wheels causes sequential wheel sectors to be advanced into and out of the associated laser treatment stations. Each wheel may include a single batch carrier carrying a single batch of dispensers, or a series of sequential batch carriers defined by sequential wheel sectors. In the illustrated embodiment of FIG. 2, six batch carriers are defined on each rotating wheel by six wheel arc sectors. Sequential batches are loaded onto the rotating wheel and advanced through the laser treatment station in sequence. It can be seen that when one batch of dispensers is being advanced out of a laser treatment station, a next batch of dispensers is being advanced into that laser treatment station. Preferably, each batch carrier holds the same number of dispensers to advance batches of the same size. The use of six batch carriers permits each wheel to rotate only one sixth of a revolution for each batch laser treatment cycle. The resulting greater wheel circumference and slower wheel rotation rate advantageously facilitates on-loading and off-loading of transport pucks onto and off of the wheel (described in more detail below).

It can be seen that each wheel can be, alternatingly, advanced to position a batch of untreated dispensers in a laser treatment station, stopped to permit each dispenser to be laser treated in the laser treatment station and advanced again to move the treated dispensers out of the laser treatment station and position a next batch of untreated dispensers in the laser treatment station. The advance coordinator (not shown) coordinates the advancement of the two wheels with the activity of the laser controller such that when the one wheel is rotating to advance a batch of untreated dispensers into its associated laser treatment station, the other rotating wheel is stationary while a batch of dispensers is being treated in its associated laser treatment station.

Preferably, the two adjacent rotating wheels rotate in opposite directions (indicated by the pair of curved arrows) to advance the dispenser batches in like direction through the alternate laser treatment stations. As shown in FIG. 2, the one wheel 140 preferably rotates counter-clockwise and the another wheel 142 preferably rotates clockwise such that the alternate batches of untreated dispensers (not shown) preferably both advance upward toward the top of the drawing. This rotation in opposition permits the laser treatment sites for treating each dispenser in the alternate batches to be arranged in mirror symmetry, which simplifies the beam deflection patterns required by beam deflector.

As shown in FIG. 2, each wheel has an associated supply path, 120 and 122, for supplying untreated dispensers from a dispenser supply (not shown). It will be appreciated that suitable means for loading of batches of dispensers onto the wheel can be adapted to operate either when the wheel is rotating or when the wheel is stationary. Preferably, as described in more detail below, loading of dispensers occurs during rotation of the wheel and, thus, occurs concurrently with the advancement of dispensers into and out of the laser treatment station associated with the same wheel (and during the time that another batch of untreated dispensers is being treated in the another laser treatment station associated with the another wheel). In any case, it can be seen from FIG. 2 that, following the loading of a batch of untreated dispensers, further rotation of the wheel will advance the batch into the associated laser treatment station. Subsequently, as described above, while the wheel is stationary with the batch of untreated dispensers in the laser treatment station, each dispenser can be treated with the laser. Following laser treatment of a batch of dispensers, further rotation of the wheel advances the treated dispensers out of the laser treatment station and concurrently advances a next batch of untreated dispensers into the laser treatment station.

Figure 3A:
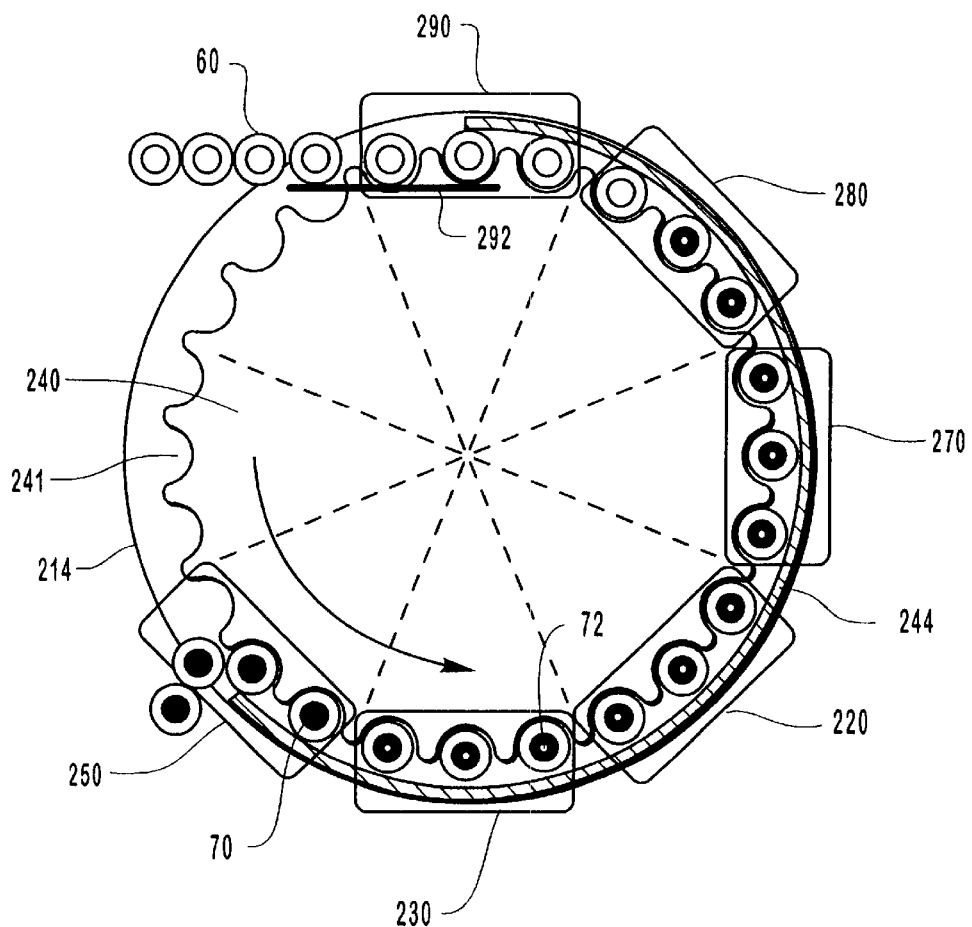
FIG. 3A is a detailed plan view of a star wheel embodiment of a rotating wheel batch carrier in accord with the present invention.

In addition to on-loading and laser treating of batches of dispensers, other processing operations may also be advantageously accomplished on batches of dispensers being carried on alternate batch carriers such as the rotating wheel batch carriers shown in FIG. 2. In order to simplify the illustrations, FIG. 3A illustrates a preferred series of processing operations occurring along the transit route of sequential batches of pharmaceutical dispensers 70 (carried in transport pucks 60) through a complete rotation of one rotating wheel 240 (similar to one of the rotating wheels shown in FIG. 2). Each processing station is illustrated as a box overlying the rotating wheel. As described in more detail below, the processing stations shown in FIG. 3A include the on-load station 250, the laser treatment station 230, an inspection station 270, a dispenser remover station 280 and a transport puck off-load station 290.

Figure 3B:
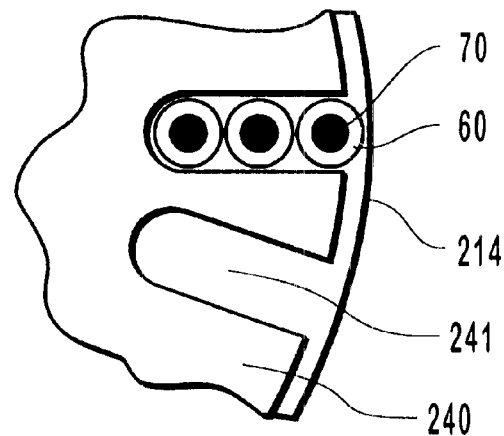
FIG. 3B is a fragmentary view of a portion of a star wheel embodiment of a rotating wheel batch carrier in accord with the present invention.
Figure 3C:
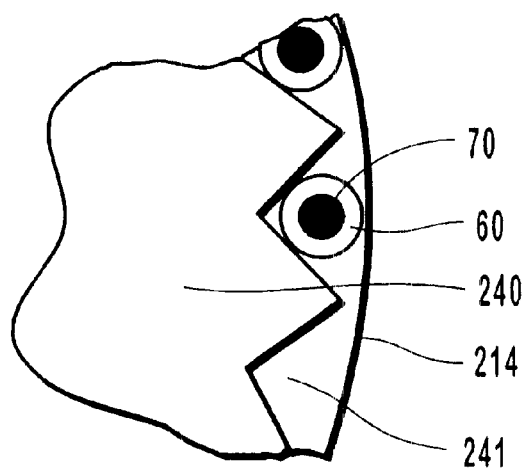
FIG. 3C is a fragmentary view of a portion of a star wheel embodiment of a rotating wheel batch carrier in accord with the present invention.

As described above, in exemplary embodiments of the present invention shown in FIGS. 3A–C, 4A–C and 5, transport pucks are preferably employed for individually transporting the exemplary elongated capsule-shaped dispensers in accord with the present invention. As best seen in the cross-section view of FIGS. 4A–C, the dispensers 70 are retained within a central bore of the transport pucks 60 to maintain a preferred attitude for laser treatment, i.e., with the small end of the dispenser containing the drill site for a drug delivery port facing upward and exposed for laser treatment. Empty transport pucks 60 (when viewed from above as in FIGS. 3A–C) are indicated by an outer circle containing a smaller inner circle. The pharmaceutical dispenser 70 (viewed from above while being transported by the transport puck) is indicated by a solid black dot residing within the inner circle of the transport puck (FIGS. 3A–C). As best shown in FIG. 3A, laser treatment of each dispenser results in a drug delivery port 72 being drilled into each dispenser, as indicated by an even smaller white dot in the center of each dispenser positioned within, and subsequent to, the laser treatment station 230. It will be appreciated, however, that other types of dispensers having different shapes may be treated with a laser in accord with the present invention. Differently-shaped dispensers may require differently-shaped transport pucks or even no transport pucks at all.

The exemplary transport puck 60 has a protective exterior structure for isolating the retained dispenser from the apparatus of the system and from the other transport pucks. The surface of the puck body is preferable a low friction material to facilitate sliding motion of the transport pucks in transit. The transport puck also has a stabilizing interior structure such as an appropriately-sized cavity within the puck body for receiving the dispenser and securely retaining the dispenser in a desired attitude for laser treatment. The surface of the puck cavity is also preferably a low friction material to permit dispensers to easily be engaged and disengaged as needed. The puck may be configured as a right cylinder having a cavity configured as a central bore through the axis of the cylinder. The symmetrical nature of the cylinder renders the transport pucks azimuth-insensitive. The vertical puck axis and vertical bore facilitate easy removal of a dispenser from the transport puck through a drop port at a dispenser remover station, if desired. The central bore may be chamfered at both ends to facilitate receiving the dispenser.

As shown in the partial plan view of FIG. 3A, the rotating wheel batch carrier preferably has a star configuration. The star wheel preferably rotates over stationary floor 214 (best shown in cross-section view of FIGS. 4A–C) to advance transport pucks (with dispensers) retained in peripheral edge voids 241. Suitable edge voids may be variously configured. For example, the edge voids may be configured as open curved indentations (shown in FIG. 3A) or open triangular indentations (shown in FIG. 3C). Relatively wide open indentations permit easy edge-on loading and edge-off off-loading of transport pucks. Alternatively, as shown in FIG. 3B, each edge void may be an open elongated slot extending into the rotating wheel configured to retain more than one transport puck in each edge void. In this manner, because each edge void on-loads and off-loads a plurality of transport pucks, the rates of loading may be increased and/or the rotation rate of the wheel may be slowed while maintaining the same general laser treatment rate.

A peripheral curb 244, extending at least partially around the wheel periphery, is preferably provided to form an outer closure for the peripheral edge voids. The curb is preferably stationary and extends from the on-load station 250 to the off-load station 290 to capture the on-loaded transport pucks (with dispensers) between the edge void and the peripheral curb during transit as the wheel rotates. The edge void and curb are configured such that each on-loaded transport puck (with dispenser) becomes securely engaged between the curb and the edge void as the wheel advances. In this manner, the batches of untreated dispensers are properly located for laser treatment, i.e., securely positioned in registration with the laser treatment sites, when the batch of dispensers is advanced into the laser treatment station.

In the embodiment of FIG. 3A, rotating wheel 240 has 24 edge voids along eight batch arc sectors, with three dispensers per batch. It will be appreciated, however, that more (or fewer) edge voids along a different number of sectors with larger (or smaller) batch sizes may also be employed.

A rotation of the wheel through each processing station is now described with reference to FIG. 3A. Transport pucks 60 carrying dispensers 70 are loaded onto the wheel at an on-load station 250 fed by the associated wheel supply path (not shown). As the wheel is advanced, the batch of untreated dispensers loaded at on-load station advance into laser treatment station 230 and are held therein for treatment with the laser beam (not shown) resulting in drug delivery ports 72 being drilled into each dispenser 70. Following laser treatment in laser treatment station 230, the transport pucks (with treated dispensers) are preferably subsequently advanced into an inspection station 270 for a determination whether each dispenser is acceptable or rejectable as described below. Next, the transport pucks (with dispensers) are advanced into a remover station 280 where the dispensers are separated from the transport pucks (as described in more detail below with reference to FIGS. 4A–C) and the now-empty transport pucks 60 are advanced into an off-load station 290 to be off-loaded from the wheel. The rotating wheel may also accommodate one or more additional stations, such as idle station 220.

Inspection station 270 is preferably provided for inspecting treated dispensers to determine whether each dispenser is acceptable or rejectable either with respect to the laser treatment or to an overall quality control standard. The inspection may involve imaging techniques in which an image of each treated dispenser is systematically compared with a reference image of an ideal or standard treated dispenser. The treated dispenser image may be a pixel image obtained by a CCD camera which captures light reflected from the dome of the dispenser. The reference image may be a pixel image retrieved from a database. The comparison may be limited to merely the presence of a drug delivery port, or may extend to the location of the port on the dome and to the size of the port or even to additional features of the dispenser. The inspection station may be located either after laser treatment station 230 or coincident with the laser treatment station as the wheel advances. The inspection station 270 associated with each wheel preferably functions in conjunction with remover station 280 to provide for separate removal of accepted and rejected dispensers. For example, an acceptance station or a rejection station, or both, may be provided either prior to or coincident with the remover station. An acceptance station would be responsive to the inspection station for collecting acceptable dispensers (with or without transport pucks) and for leaving the rejectable dispensers to be removed at the remover station. Alternatively, a rejection station could be provided responsive to the inspection station for discarding the rejectable dispensers (with or without transport pucks) and for leaving the acceptable dispensers to be removed at the remover station. These stations may be similar in principle and operation to remover station 280 as described in more detail below with reference to FIGS. 4A–C.

An off-load station is preferably associated with each wheel for off-loading empty transport pucks. As shown in FIG. 3A, off-load station 290 may employ off-load guide 292 for nudging the empty transport pucks out of the edge voids and radially away from the rotating wheel. Preferably, each empty transport puck is off-loaded along a straight line path generally tangent to the rotating wheel thereby permitting the transport pucks to off-load without a change in direction of motion. As described in detail below (see FIG. 5), the empty transport pucks are preferably recycled and reused for transporting subsequent dispensers. Off-load guide 292 comprises any suitable structure such as a straight edge guide or cam projecting at a shallow low angle relative to the curved path of the edge voids mounted just above the upper surface of the rotating wheel to engage the upper portion of the body of each transport puck as the transport pucks pass through the off-load station. The off-load guide 292 is preferably positioned to begin in a region just inside the edge voids, extend obliquely across the path of the edge voids, and end at the periphery of the rotating wheel such that transport pucks are gradually swept radially out of the edge voids and off the rotating wheel.

Figure 4A:
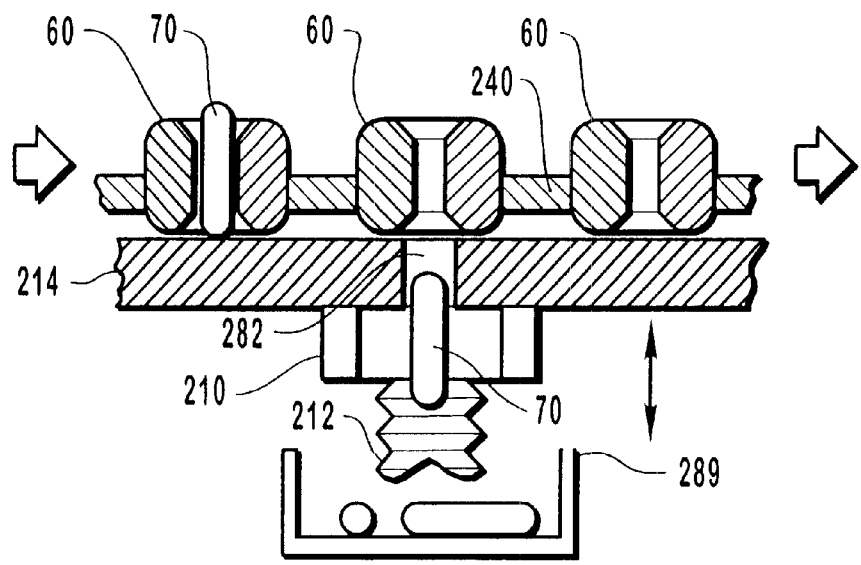
FIG. 4A is a fragmentary view in section of a remover station portion of a star wheel embodiment of a rotating wheel batch carrier in accord with the present invention.

Turning now to FIG. 4A, a partial cross-section view of the curved edge of the rotating wheel 240 taken along the central bores of the transport pucks as viewed toward the center of rotating wheel 240 is shown. The edge view includes three edge voids retaining three transport pucks in the process of passing remover station 280. Stationary floor 214, under rotating wheel 240, is slidingly engaged with the bottoms of the transport pucks and dispensers to provide support as the wheel rotates. Remover station 280 may have remover port 282 formed in the stationary floor 214 at the remover station to facilitate removal of treated dispensers from the rotating wheels. In the embodiment shown in FIG. 4A, the port is a gravity drop port, and the treated dispensers are passively removed from the batch carrier sector on the rotating wheel automatically by the force of gravity. The treated dispensers drop out of the central bore of the transport puck and down through the drop port when the dispensers pass over the drop port as the batch carrier sector advances past the remover station. The transport pucks advance from left to right (indicated by horizontal arrows shown in FIG. 4A). A transport puck 60 directly over the drop port 282 dropping a dispenser 70 down through the drop port into collector 289, a next transport puck (with dispenser) and an empty transport puck that has passed the drop port and has already dropped its dispenser are shown.

Figure 4B:
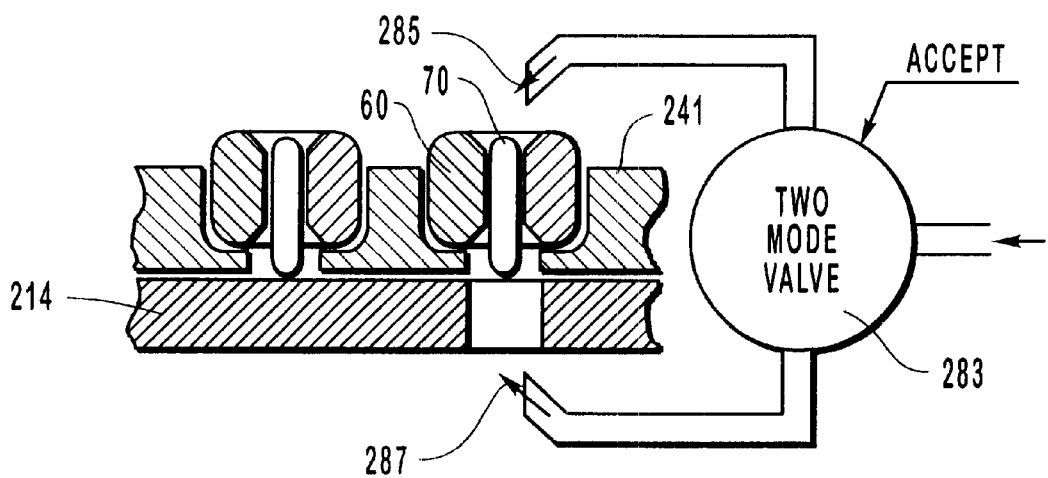
FIG. 4B is a fragmentary view in section of remover station portion of a star wheel embodiment of a rotating wheel batch carrier in accord with the present invention.

If desired, the remover station may employ an active mechanism which actively displaces or "purges" treated dispensers from the transport pucks as the batch carrier sector advances past the remover station. The removal force may act either upwards or downwards on the treated dispensers. The active mechanism may be a high-pressure downward blast of purging air 285 as shown in FIG. 4B. The air pushes the dispensers from above in a downward direction through the port. Alternatively, the active mechanism may be an upward blast of purging air 287 which pushes the dispensers from below in an upward direction off of the rotating wheel.

In a preferred embodiment, both a downward blast and an upward blast may be employed in the alternative at the same remover station by two mode valve 283 connected to a pressurized air supply (not shown). In this manner, dispensers may be alternately removed upwardly or downwardly in response to a determination of the acceptability of the dispenser performed at the inspection station as described above. For example, the valve may be maintained in a default blast position (either upward or downward) to reject all dispensers, until an ACCEPT command from the inspection station sets the valve temporarily to the opposite blast position. The two-mode valve is preferably biased towards rejection over acceptance by the rejection default priority to guard against false acceptance. Alternatively, the air supply may be a low pressure or partial vacuum active force instead of a high-pressure force, which pulls the dispensers out of the transport pucks rather than pushing the dispensers with a high-pressure blast. With either an air blast or an air vacuum, the dispensers may be removed while the rotating wheel is advancing. A full stop is not required.

It will be appreciated that other suitable means for removing the dispensers from the transport pucks may also be utilized. For example, an alternative active mechanism such as an upward purging plunger for pushing the dispenser upward out of the wheel and/or a downward purging plunger for pushing the dispenser downward may be employed. Different active mechanisms may be combined or utilized along with the gravity drop port feature. For example, upward action of a plunger may be responsive to an ACCEPT command from the inspection station to accept a dispenser while rejected dispensers are gravity dropped downward through the port.

It will be appreciated that a batch of air blasts or batch of plungers may be employed in unison to remove an entire batch of treated dispensers simultaneously at the remover station. The active force facilitates removal of dispensers that may become lodged in the transport puck. A dispenser may be "cocked" or tilted within the central bore of the transport puck and jammed against the sides of the bore. A dispenser may be slightly out-of-round, or have a slightly enlarged in diameter, or become coated with debris removed from the dispenser during laser treatment. These dispensers may become loosely stuck in the central bore and require an active force to dislodge them.

Because dispensers may be manufactured in different sizes, it is preferable to provide means for adjusting the wheel to accommodate differently-sized dispensers at the laser treatment station. Such means may include, for example, adjustment means for raising or lowering the position of the dispensers to thereby achieve the correct distance between the laser beam and the treatment site(s) on each dispenser. Such an adjustment permits the wheel to be used for laser treating dispensers having different heights without necessarily having to adjust the position of the laser beam. The laser treatment of the dispensers is most efficient when the treatment site(s) are coincident with the focal point of the laser beam. At the focal point, the beam is concentrated into the smallest cross-section with the greatest energy per square unit. This concentrated beam burns the smallest hole to the greatest depth in the shortest time. Assuming that the focal point of the laser beam is coincident with the desired treatment site on "standard" size dispensers, if dispensers that are taller or shorter than the standard size are to be treated, the treatment site on the dispensers will not coincide with the focal point. In such circumstances, it would be desirable to be able to adjust the position of the dispensers to regain that coincidence.

One manner in which such adjustments may be made is to provide a suitable wheel adjustment mechanism such as support nut 210 and threaded center post 212, shown in cross-section in FIG. 4A. Stationary floor 214, under rotating wheel 240, rests on the support nut such that adjustments to the position of the support nut on the center post can be used to suitably raise or lower the stationary floor as needed to accommodate dispensers having different heights. The rotating wheel is adapted to be movable along with the stationary floor, if desired. For example, the rotating wheel may be spaced from the stationary floor by a center bushing (not shown) that is turned by a drive stem (not shown) within the center post. In this manner, both the stationary floor and the rotating wheel are adjusted by moving the position of the support nut to thereby raise or lower the transport puck 60 and the dispenser 70 carried therein.

Alternatively, the rotating wheel may be affixed to the center post such that only the height of the stationary floor is adjusted when the support nut is turned. As shown in FIG. 4B, the rotating wheel 241 may be adapted to support each transport puck 60 at a fixed height while permitting the dispenser 70 carried therein to rest on the stationary floor. Now, as the floor is raised or lowered, the dispenser is also raised or lowered relative to the transport puck and the rotating wheel.

It will be appreciated that, except for the laser treatment stations in which the dispenser batches are held stationary during laser treatment, the other stations, i.e., the on-load station, the inspection station, the remover station and the off-load station, may be adapted to operate during the time that the rotating wheel is moving a batch sector through that station or during the time that the rotating wheel is held stationary with a batch sector positioned in that station. Accordingly, while one rotating wheel is held stationary to permit laser treatment of a batch of dispensers in the associated one laser treatment station, some or all of the other stations associated with the one wheel may also be operating and, at the same time, the another rotating wheel is advancing, i.e., rotating, to position a batch of dispensers in the associated another laser treatment station while, similarly, some or all of the other stations associated with the another wheel may also be operating.

In addition to coordination of the advancing of one batch of untreated dispensers into one laser treatment station with the laser treatment of another batch of untreated dispensers in an another laser treatment station, the supply of untreated dispensers is also preferably controlled such that a substantially continuous supply of untreated dispensers for batch loading and sequential advancement into the laser treatment stations is maintained. Suitable methods and apparatus for maintaining a substantially constant supply to the alternate batch carriers of the present invention can be provided, for example, with appropriate feedback monitoring and rate coordination logic circuitry provided at appropriate locations between the dispenser supply and the supply paths for each batch carrier.

Figure 5:
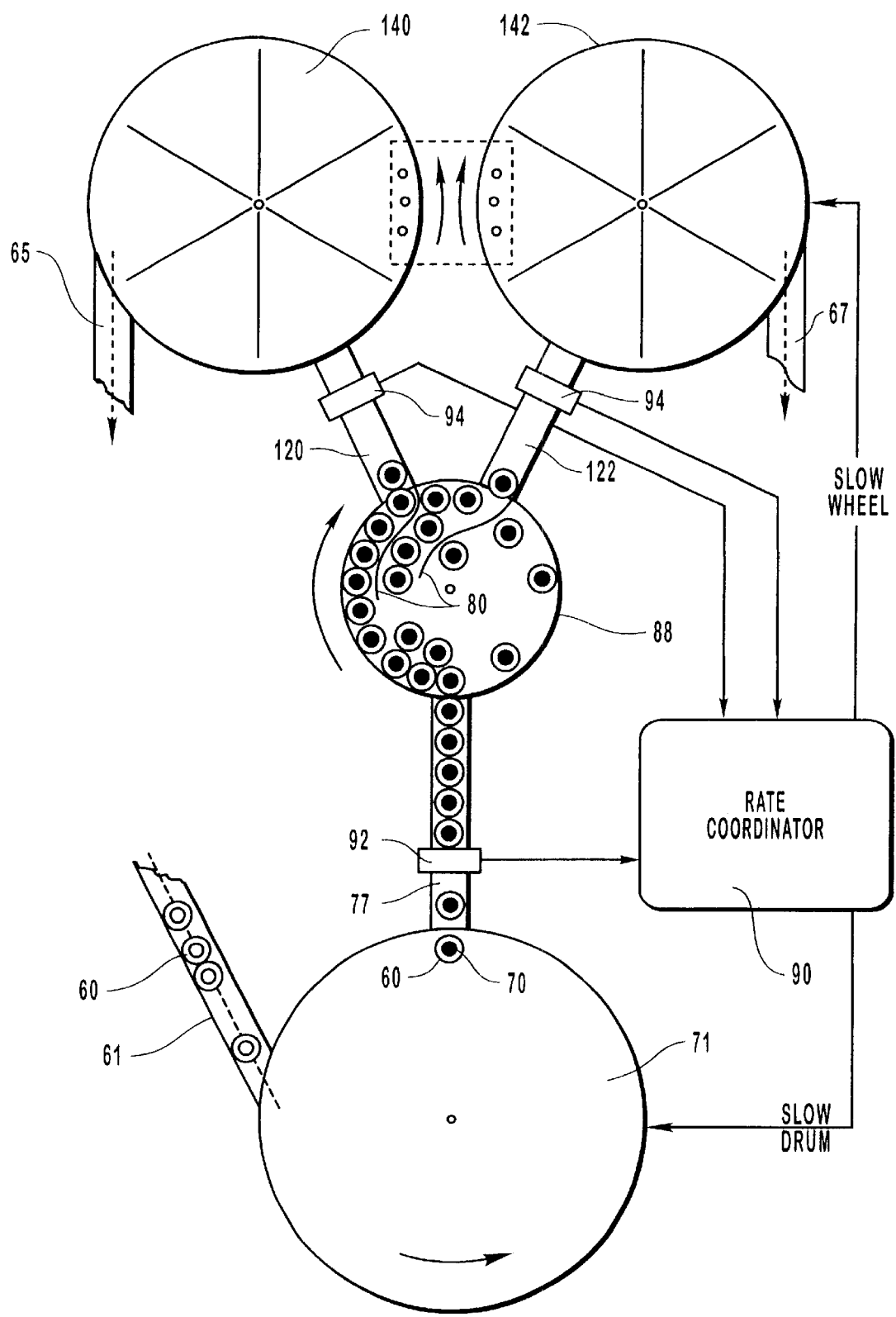
FIG. 5 is a plan view of a preferred dispenser distribution and supply system in association with the preferred embodiment of the present invention having two rotating wheel batch carriers as shown in FIG. 2.

FIG. 5 illustrates a preferred dispenser distribution and supply system in association with the preferred embodiment of the present invention having two rotating wheel batch carriers as shown in FIG. 2. Details of the operations that occur during rotation of the wheels have been described above with reference to FIGS. 2 and 3A. Accordingly, FIG. 5 illustrates the distribution and supply of transport pucks and dispensers up to the rotating wheels. As shown in FIG. 5, a transport puck supply path 61 supplies empty transport pucks 60 to be mated with dispensers provided from a central dispenser supply such as a rotating supply drum 71 or other suitable sorting device. At the supply drum 71, individual dispensers are separated from a bulk source of dispensers and inserted into individual transport pucks (not shown) and fed to central supply path 77 for transport to the multiple wheel supply paths 120 and 122 (indicated in dashed lines). Preferably, one wheel supply path is associated with each of the multiple rotating wheels.

The multiple rotating wheels collectively have a general treatment rate for treating the dispensers, and the supply drum 71 has a general supply rate for supplying the transport pucks (with dispensers). To facilitate a substantially continuous supply of dispensers to the alternate batch carriers, 140 and 142, the general supply rate is preferably maintained to be slightly greater than the general treatment rate. One aspect of this supply rate greater than treatment rate feature is preferably provided by a reserve supply accumulator 88 located between the supply drum and the wheel supply paths as shown in FIG. 5. Transport pucks carrying dispensers travel the central supply path 77 to supply accumulator 88 where the central supply of transport pucks (with dispensers) is preferably separated into multiple smaller wheel supplies of transport pucks (with dispensers) and directed into the multiple wheel supply paths. As shown in FIG. 5, suitable directing means such as diverger gates 80 are used to divide the central supply in the supply accumulator 88 into multiple wheel supplies for each wheel supply path. The hub configuration of supply accumulator 88 provides storage capability for receiving and accumulating reserve transport pucks (with dispensers). Supply accumulator 88 preferably has a revolving accumulation floor (with a direction of movement indicated by the curved arrow) surrounded by stationary peripheral wall. The wall has multiple peripheral outlets and each outlet is aligned with a diverger gate 80 for supplying a wheel supply path.

The reserve transport pucks (with dispensers) collect within the supply accumulator 88 forming a reserve supply for the rotating wheels. This reserve promotes a constant supply of transport pucks (with dispensers) to the rotating wheels and minimizes the occasion for reducing the dispenser treatment rate. Advantageously, the accumulator is compact and does not require an extended path length to store the reserve.

It will be appreciated that the supply accumulator is optional. If desired, the transport pucks (with dispensers) may be supplied directly from the supply drum 71 to the wheel supply paths by means of a series of individual divergers aligned with a central supply path wherein each diverger services one wheel supply path. For example, the transport pucks (with dispensers) may travel from the supply drum in a single file column with alternate pucks diverted to alternate rotating wheels by alternate divergers or the transport pucks (with dispensers) may travel in multiple file columns with alternate columns diverted to the alternate wheels, i.e., in the two-wheel embodiment, the transport pucks may be in double file with two columns, one column diverted to each of the two wheel paths.

To further facilitate a substantially continuous supply of dispensers to the alternate batch carriers, 140 and 142, another aspect of the supply rate greater than treatment rate feature is preferably provided by a rate coordinator 90 for controlling the treatment rate and the supply rate by sending rate commands to the wheels and to the drum. This supply rate greater than treatment rate relationship produces an expanding supply backlog of transport pucks (with dispensers) being supplied to the supply accumulator 88 for supporting the general treatment rate of the rotating wheels.

The presence of the supply backlog permits the supply drum and the rotating wheels to operate within a range of independent rates. In this manner, variations in the supply rate caused by surges and delays within the supply drum do not affect the treatment rate of the rotating wheels. Similarly, spurts and jams within the rotating wheels do not affect the supply rate of the drum. Accordingly, any periodic uneven flow of transport pucks (with dispensers) introduced by loading of each batch onto the alternate rotating wheels will be ameliorated by the combined effects of the supply accumulator's capacity to absorb some backlog and, if needed, by the rate controller's capacity to adjust the supply backlog from the supply drum 71.

It will be appreciated that the rate coordinator 90 can be any suitable device comprising appropriate logic circuitry and having appropriate connections to receive signals from various detectors strategically located to monitor the supply rates and treatment rates and to generate signal commands to effect changes in the speeds of the supply drum and/or the rotating wheels. Such rate coordinators are known in the art and may use, for example, a maximum supply backlog detector 92 responsive to an expanding supply backlog on the central supply path for temporarily reducing the general supply rate of the supply drum. This reduction prevents the supply backlog from expanding above a predetermined maximum backlog size. An excessive backlog may cause transport pucks to back-up along the supply path into the supply drum and interfere with the operation of the drum.

Maximum supply detector 92 may be any suitable presence (or absence) monitoring device such as a light beam across the supply path from a light source on one side to a light sensor on the other. For example, when the transport pucks passing the supply detector are not in backlog, the progression of transport pucks is spaced apart on the supply path. Short flashes of light passing through these spaces keep the supply detector in a deactivated condition. As the supply backlog expands along central supply path towards supply accumulator 88, however, the transport pucks passing the supply detector become jammed together, closing the space between adjacent transport pucks and blocking the light beam. The absence of the light flashes activates maximum supply backlog detector 92, which sends a BACKLOG signal to rate coordinator 90. The rate coordinator issues a SLOW DRUM command to supply drum 71 which reduces the rate of supply which in turn contracts the supply backlog. When the supply backlog has contracted sufficiently, spaces reappear in the progression of transport pucks, causing maximum supply detector to deactivate and terminate the BACKLOG signal. Thus the central supply of dispensers to the rotating wheels is maintained without interrupting the operation of the rotating wheels.

For various mechanical reasons, the general supply rate may temporarily become less then the general treatment rate, causing the supply backlog to spontaneously contract. Accordingly, the rate coordinator may also utilize a minimum supply backlog detector responsive to the contracting supply backlog on the supply path for temporarily reducing the rotation speed (and, thus, the general treatment rate) of the rotating wheels. This reduction prevents the supply backlog from contracting below a predetermined minimum backlog size. An inadequate backlog along the wheel path may cause loading failure at the on-load station resulting in a "short" batch and empty treatment sites at the laser treatment station. Preferably, the minimum number of transport pucks maintained in each wheel supply backlog is greater than the number of dispensers that comprise a batch of dispensers. Such an adequate on-load backlog permits an entire batch of transport pucks (with dispensers) to be smoothly loaded onto a rotating wheel without interruption due to a lack of transport pucks in the on-load backlog.

As shown in FIG. 5, minimum supply backlog detectors 94 are preferably positioned to monitor the supply for each rotating wheel. Each minimum supply detector 94 may be any suitable presence (or absence) monitoring device similar in principle and operation to maximum supply detector 92 but with the reverse relationship between the supply backlog and activation. For example the presence of a supply backlog maintains the minimum detector deactivated, and the loss of the supply backlog activates the minimum detector. The absence of light flashes through the spaces between the adjacent transport pucks keeps the minimum detector deactivated. As the supply backlog contracts, the spaces appear between the transport pucks passing flashes of light. The light flashes activate minimum supply backlog detector 94, which sends a NO BACKLOG signal to rate coordinator 90. The rate coordinator issues a SLOW WHEEL command to the rotating wheels reducing the rate of treatment causing the supply backlog to expand.

The above-described use of maximum supply detector 92 and minimum supply detector 94 facilitates maintenance of a supply backlog and supply back pressure within an effective operating range. Activating either of the supply detectors in response to a change in supply backlog, temporarily slows either the supply drum or the rotating wheels, avoiding overdrive difficulties associated with an increase in speed. Although the use of one maximum supply detector for the central supply path and one minimum supply detector for each wheel supply path is shown, it will be appreciated that additional maximum and/or minimum backlog detectors as described above can also be employed at various locations along the central supply path and/or wheel supply paths to provide additional feedback information and more rigorous rate-controlling response through rate coordinator 90. For example, if desired, both a maximum backlog detector and a minimum backlog detector could be used in each path.

Central supply drum 71 may have an optimum operating speed, which is temporarily reduced to zero by maximum supply detector during an expansion of the supply backlog. Alternatively, the supply drum may have a variable operating speed, which is temporarily reduced to a slower speed by maximum supply detector. Similarly, rotating wheels 140 and 142 may each have an optimum operating speed which is temporarily reduced to zero by minimum supply detector during a contraction of the supply backlog, or a variable operating speed which is temporarily reduced to a slower speed. Variable operating speeds that are temporarily reduced are preferred to avoid the difficulties of restarting motion from a dead stop. A central clock in rate coordinator 90 may control the operating speed of each portion of the system. The amount of laser energy delivered to treat each dispenser is unaffected by any changes in operating speed.

In the preferred embodiment shown in FIG. 5, on-load stations 150 and 152 associated with each rotating wheel, 140 and 142 and aligned with each associated wheel supply path, 120 and 122, respectively, are employed for on-loading untreated dispensers onto a batch carrier sector of the associated wheel (as shown in FIG. 2). The on-load stations are located before the laser treatment station as the wheel advances, and provide the location where transport pucks with untreated dispensers are loaded on a batch carrier sector as that sector is advanced through the on-load station.

Suitable path drivers for transporting the transport pucks and dispensers are known in the art. For example, a suitable supply path driver such as a traction belt may be utilized for paths such as central supply path 77 and wheel supply paths 120 and 122 to facilitate a supply back pressure in these paths. The supply traction belt may be an endless type conveyer belt that is driven by suitable power rollers and idler rollers. The supply back pressure urges the supply backlog along the central supply path toward the accumulator and along the wheel supply paths toward the rotating wheels for treatment. The supply traction belt conveys the transport pucks (with dispensers) such that each conveyed transport puck joins the supply backlog and adds an incremental back pressure to the supply back pressure. The supply traction belt driver provides direct traction under the transport pucks and dispensers for conveying them to the supply backlog, and then provides slipping traction under the conveyed transport pucks and dispensers for creating the supply back pressure. The slipping traction generates the supply back pressure and functions as a supply clutch, eliminating a direct connection between the drum supply of transport pucks and the accumulating supply backlogs. The transport pucks at the tail of the supply backlog push the transport pucks at the front of the supply backlog. This forward pressure moves the front transport pucks into the supply accumulator and/or onto a rotating wheel at the on-load station, as described elsewhere, and across other non-drive sections of the supply path. The instantaneous value of the supply back pressure is a function of the instantaneous number of transport pucks within the supply backlog being urged by the driver at any instant. Each transport puck being urged at any instant contributes an incremental back pressure to the supply back pressure, and the instantaneous value of the supply back pressure is the sum of these incremental back pressures. Preferably, the motion of the supply traction belt is generally constant to provide smooth conveying and a generally constant incremental back pressure from each transport puck (with dispenser) on the supply traction belt.

Preferably, empty transport pucks are off-loaded from the rotating wheels, recycled and reused. For this purpose, transport puck collector paths, 65 and 67, one associated with each rotating wheel, are provided to collect the empty pucks and recycle these back into the puck supply feeding puck supply path 61. To ensure that the used transport pucks have a clear bore for receiving a new dispenser, means for inspecting each puck and for ejecting any unsuitable transport pucks (not shown) are preferably provided. For example, inspection may be accomplished by known in the art methods such as by directing a "through" light beam through the central bore of each transport puck from one side of the transport puck to a light sensor on the other side. Preferably, the diameter of the light beam is greater than the diameter of the bore, passing a predetermined quantity of light if the bore is "clear". An "unclear" bore may be damaged or may contain a dispenser or a dispenser fragment or debris such that the quantity of light passing is less than the predetermined quantity. In this case, the light sensor detects the lower light level and ejects the "unclear" transport puck. The ejection force may be achieved through methods known in the art such as a blast of air across the return path forcing the detected transport puck and dispenser to the side.

Suitable path drivers such as moving traction belts are preferably associated with the transport puck collector paths 65 and 67 to provide an off-load back pressure urging the off-load backlog along the collector path and with the puck supply path 61. These traction belts may be similar in principle and operation to supply traction belts as described above with reference to the central supply path and the wheel supply paths. Also, as described above, maximum and/or minimum off-load backlog detectors can be employed along puck collector paths 65 and 67 to provide appropriate feedback and response through rate coordinator 90 to prevent expansion of the off-load backlog above an amount that could interfere with the treatment rate of the associated rotating wheel. If desired, backlog detectors may also be employed along puck supply path 61 to provide appropriate feedback and response through rate coordinator 90 to prevent expansion of the puck supply backlog above an amount that could interfere with the off-loading of empty pucks from the rotating wheels.

METHOD OF TREATMENT

A preferred method of controlling the supply of batches of pharmaceutical dispensers, advancing batch carriers on rotating wheels, and treating batches of dispensers thereon with a beam of laser energy, with reference to preferred embodiments of the apparatus of the present invention as described hereinbefore is now described. Note that a two-treatment wheel embodiment has one wheel (the first wheel) and another wheel (the second wheel) and one laser treatment station and another laser treatment station associated, respectively, with the one and the another wheel. In a three (or more) wheel embodiment, the "one and another" refers to any one and any another of the wheels and is not limited to a first and a second wheel or second and third, etc. The basic steps and additional steps of the method and the execution of the repeating batch cycle are presented below.

Providing a central supply of transport pucks each transporting a dispenser for treatment from the central supply drum at a general supply rate;

Diverging the central supply of transport pucks (with dispensers) into multiple smaller wheel supplies of transport pucks (with dispensers), one wheel supply for each treatment wheel;

Loading batches of untreated dispensers onto alternate (one and another) batch carriers, each batch carrier comprising a rotating wheel;

Rotating each wheel to load sequential batches of untreated dispensers and to advance sequential batches of untreated dispensers into and out of the associated (one and another) laser treatment stations; and Treating each dispenser in sequential batches of untreated dispensers as these batches are alternatingly advanced into the alternate laser treatment stations.

The rotating (to advance batches of dispensers) and stopping (during laser treatment of dispensers) cycle of one wheel is coordinated to alternate with the rotating and stopping cycle of the another wheel such that the laser beam is optimally substantially continuously presented with one or another batch of dispensers for laser treatment in order to maximize the rate of laser treatment of the dispensers.

The above general method may include the following additional steps:

Loading untreated dispensers onto advancing batch carriers during each rotating step of the repeating batch cycle;

Inspecting treated dispensers after each stopping step of the repeating batch cycle, to determine whether each dispenser is acceptable or rejectable;

Removing the treated dispensers from the transport pucks on an advancing batch carrier during each rotating step of the repeating batch cycle;

and off-loading and recycling empty transport pucks. In addition, the method preferably provides for maintaining the general supply rate for supplying the dispensers to the treatment wheels at a greater rate than the collective general treatment rate for treating the dispensers. The supply rate greater than treatment rate relationship produces a supply backlog of transport pucks with dispensers for supporting the general treatment rate of the treatment wheels.

While there has been described and pointed out features and advantages of the invention, as applied to exemplary embodiments, those skilled in the art will appreciate that various modifications, changes, additions, and omissions in the descriptions within the specification can be made without departing from the spirit of the invention. Therefore, the scope of the invention is to be determined by the terminology of the following claims and the legal equivalents thereof.

We claim:

1. An apparatus for treating pharmaceutical dispensers with a beam of laser energy, the apparatus comprising:

a plurality of laser treatment stations;

a laser source for providing the beam of laser energy to treat pharmaceutical dispensers positioned in said plurality of laser treatment stations;

a laser beam controller configured to direct the beam of laser energy to alternatingly operate in each of said plurality of laser treatment stations;

a plurality of batch carriers, each batch carrier adapted to carry a series of sequential batches of untreated pharmaceutical dispensers into and out of said plurality of laser treatment stations; and an advance coordinator configured to advance each of said plurality of batch carriers within said plurality of laser treatment stations in a repeating, alternating cycle, said repeating, alternating cycle being in coordination with the activity of the laser controller such that a batch of untreated pharmaceutical dispensers is substantially continuously positioned in one or another of said plurality of laser treatment stations.

2. the apparatus of claim 1, wherein the plurality of laser treatment stations are symmetrical within a common focal plane with respect to said laser beam.

3. The apparatus of claim 2, wherein the plurality of batch carriers are positioned to obtain a region of adjacency that encompasses said plurality of laser treatment stations.

4. The apparatus of claim 3, wherein each batch carrier comprises a linear conveyor, each linear conveyor carrying pharmaceutical dispensers arrayed in repeating batch configurations.

5. The apparatus of claim 3, wherein each batch carrier comprises a rotating wheel, each rotating wheel carrying pharmaceutical dispensers arrayed in repeating batch configurations delimited by sectors of the wheel, said sectors having a size that permits a single batch to be located in each laser treatment station as each sector rotates into the region of adjacency.

6. The apparatus of claim 5, wherein the plurality of batch carriers comprises two rotating wheels and the plurality of laser treatment stations comprises two stations.

7. The apparatus of claim 6, wherein one of the rotating wheels rotates clockwise and the other rotating wheel rotates counter-clockwise.

8. The apparatus of claim 7, further comprising a dispenser on-loading station associated with each rotating wheel for on-loading batches of untreated pharmaceutical dispensers onto sequential sectors of the wheel.

9. The apparatus of claim 8, further comprising a dispenser removing station associated with each rotating wheel for removing treated pharmaceutical dispensers from the rotating wheel.

10. The apparatus of claim 9, further comprising a stationary floor under each rotating wheel.

11. The apparatus of claim 10, wherein each removing station comprises a port through the stationary floor through which treated pharmaceutical dispensers are passively removed by gravity.

12. The apparatus of claim 10, wherein each removing station comprises an active mechanism which actively removes treated pharmaceutical dispensers.

13. The apparatus of claim 9, further comprising an inspection station associated with each rotating wheel for determining whether treated pharmaceutical dispensers are acceptable or rejectable.

14. The apparatus of claim 9, further comprising a transport puck for each individual pharmaceutical dispenser which retains that pharmaceutical dispenser and transports that pharmaceutical dispenser into the apparatus at the on-load station and through the one of said plurality of laser treatment stations for treatment and through one of the removing stations for removal of treated pharmaceutical dispensers from the transport puck.

15. The apparatus of claim 14, further comprising an off-load station associated with each rotating wheel for off-loading empty transport pucks.

* * * * *